United States Patent [19]
Bühler et al.

[11] Patent Number: 5,762,872
[45] Date of Patent: Jun. 9, 1998

[54] APPARATUS FOR CHEMICAL AND BIOCHEMICAL ANALYSIS OF SAMPLES

[75] Inventors: Jürg Bühler, Rothenburg; Andreas Greter, Steinhausen, both of Switzerland

[73] Assignee: Hoffmann-La Roche Inc., Nutley, N.J.

[21] Appl. No.: 899,461

[22] Filed: Jul. 23, 1997

Related U.S. Application Data

[63] Continuation of Ser. No. 645,547, May 10, 1996, abandoned, which is a continuation of Ser. No. 528,074, Sep. 14, 1995, abandoned, which is a continuation of Ser. No. 187,926, Jan. 27, 1994, abandoned, which is a continuation of Ser. No. 41,301, Mar. 31, 1993, abandoned.

[30] Foreign Application Priority Data

Apr. 6, 1992 [EP] European Pat. Off. ............ 92105903.6

[51] Int. Cl.$^6$ .................................................... G01N 35/02
[52] U.S. Cl. ............................. 422/64; 422/63; 422/67; 436/43; 436/48
[58] Field of Search .............................. 422/63, 64, 65, 422/67, 100, 103, 104; 436/43, 47, 48, 49, 180

[56] References Cited

U.S. PATENT DOCUMENTS 3,115,966 12/1963 Leiter .
3,322,958 5/1967 Heiss et al. .
3,432,049 3/1969 Howells et al. .
3,644,095 2/1972 Netherler et al. .
4,582,990 4/1986 Stevens .
4,699,766 10/1987 Yamashita et al. .
4,785,407 11/1988 Sakagami .
4,844,868 7/1989 Rokugawa .
4,861,553 8/1989 Mawhirt et al. .
4,919,887 4/1990 Wakatake .
5,066,135 11/1991 Meyer et al. .

FOREIGN PATENT DOCUMENTS 99.103 7/1983 European Pat. Off. .
92.105901 4/1984 European Pat. Off. .
92.105902 4/1984 European Pat. Off. .
92/05448 4/1992 WIPO .

*Primary Examiner*—Long V. Le
*Attorney, Agent, or Firm*—George W. Johnston; William H. Epstein; John P. Parise

[57] ABSTRACT

The analytical device comprises a conveyor for conveying cuvettes to one or more stations for processing samples for analysis in the cuvettes. The processing stations comprise means for removing individual cuvettes from the conveyor, transferring the cuvettes to a processing position and returning the cuvettes to the conveyor after processing.

2 Claims, 2 Drawing Sheets

APPARATUS FOR CHEMICAL AND BIOCHEMICAL ANALYSIS OF SAMPLES

This is a continuation of application Ser. No. 08/645,547, filed May 10, 1996, which is a Rule 60 Continuation of Ser. No. 08/528,074 filed Sep. 14, 1995, which is a Rule 60 Continuation of Ser. No. 08/187,926, filed Jan. 27, 1994, which is a Rule 60 Continuation of Ser. No. 08/041,301, filed Mar. 31, 1993, all now abandoned.

FIELD OF THE INVENTION

The invention relates to a device for chemical and biochemical analysis, comprising a conveyor for conveying cuvettes and one or more stations for processing the samples for analysis in the cuvettes.

BACKGROUND OF THE INVENTION

Automatic analytical devices usually operate on the following principle: samples for analysis or parts of samples are placed in containers and then subjected to a series of processing steps such as adding (pipetting) reagents, mixing, incubation, and the like, and measurements of the reactions which have taken place are either made a number of times during processing or once at the end of processing. The usual procedure is as follows: the containers holding the samples for analysis are placed in a fixed sequence on a conveyor and travel through various processing stations, or in the case of "batch processing", as is usual in the case of "centrifugal analysers", all sample containers are placed on a carrier (rotor) and subjected practically simultaneously to the processing steps and measurements. Analytical systems operating on these principles give good service in large clinics and analytical centres where large numbers of samples have to be processed.

In view, however, of the variety of possible analyses today and the medical requirements, particularly in clinical chemistry, it has been found that the automatic analysers conventionally used before for large quantities of samples are not sufficiently flexible to provide analytical profiles (full random access) specifically adapted to individual patients or medical conditions, while still being able to handle a large number of samples from patients.

SUMMARY OF THE INVENTION

The object of the invention therefore is to provide an analytical system in which a large number of analytical samples can be processed with very great flexibility with regard to the analytical profile obtained from the individual sample.

This is achieved according to the invention which relates to a device for chemical and biochemical analysis, comprising a conveyor for conveying cuvettes and one or more stations for processing the samples for analysis in the cuvettes, characterized by means (4) for removing individual cuvettes from the conveyor (2), for transferring the cuvettes to a position for processing and for returning the cuvettes to the conveyor after processing.

BRIEF DESCRIPTION OF THE DRAWINGS

The invention is described below with reference to the accompanying drawings, in which.

DETAILED DESCRIPTION THE PREFERRED EMBODIMENTS

The invention relates to a device for the chemical and/or biochemical analysis of one or more individual samples, comprising:

a) one or more individual cuvettes each having an individual sample therein;

b) one or more processing stations;

c) conveyor means for conveying individual cuvettes to a processing station;

d) removal means for removing individual cuvettes from the conveyor means and placing the removed individual cuvette in a predetermined position in the processing station;

e) processing means for processing the sample in the removed individual cuvette; and f) return means for returning the removed individual cuvette to the conveyor means after the sample in the cuvette has been processed at the processing station.

Figure 1:
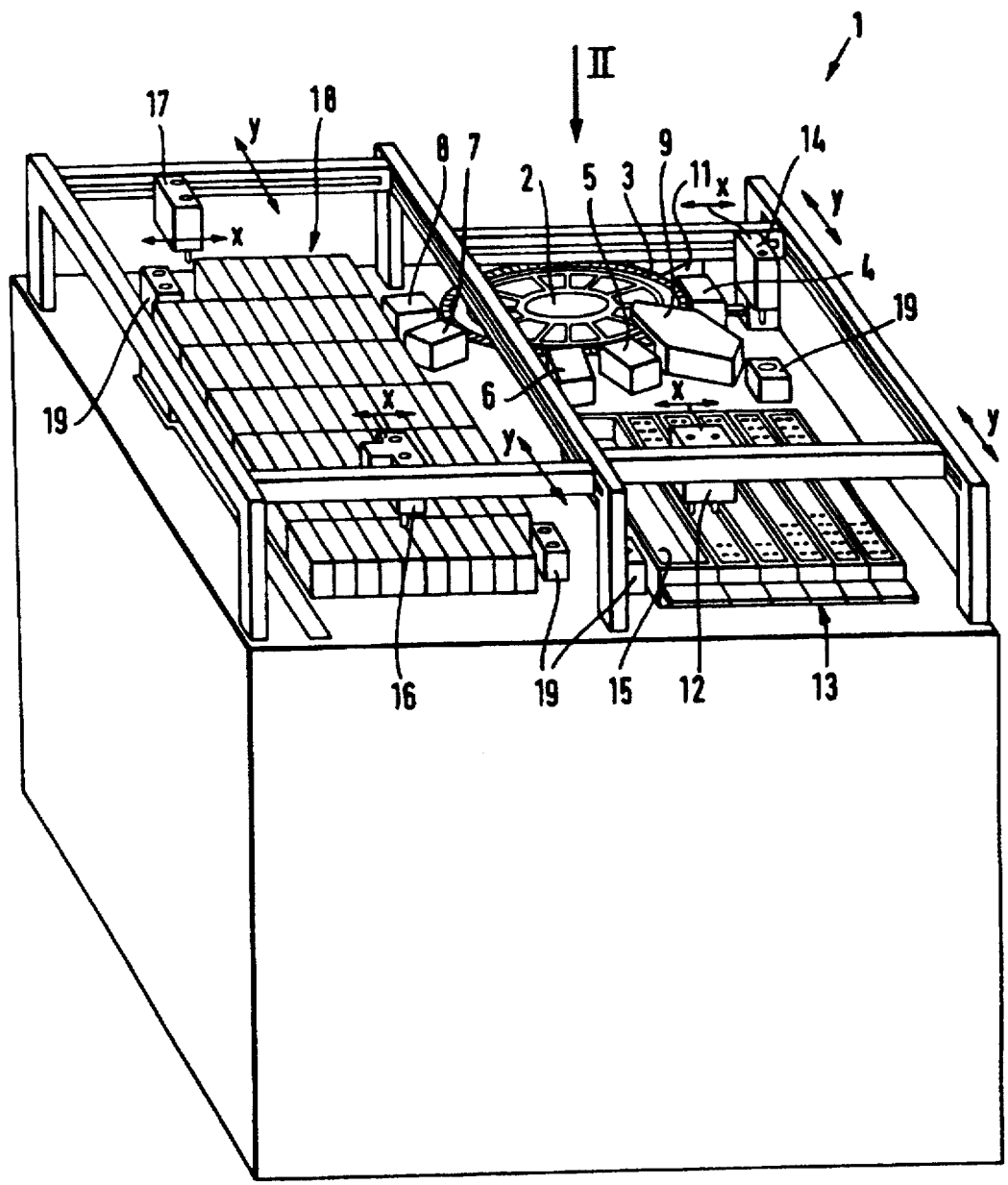
FIG. 1 is an axonometric overall view of an analytical device.

As shown in FIG. 1, the device 1 comprises a closed substructure 10 having a top surface on which a number of functional devices are disposed. The substructure contains all the devices which are only indirectly connected with the actual analytical processes, for example, electricity supply, electronics, cuvette supply and disposal means, refrigerating devices and the like.

On the top surface, there is a first region 18 in which all reagents are kept available for pipetting, and a second region 13 for disposing the containers from which the samples are pipetted into the measuring cuvettes and a third region which is the actual analytical region.

Conveyor means 16, 17 each being apt to convey one or preferably two pipetting needles of a pipetting device to desired pipetting positions are arranged for displacements above the first region 18 in order to enable pipetting of predetermined amounts of the reagents disposed in that region.

Conveyor means 12, 14 each being apt to convey one or preferably two pipetting needles of a pipetting device to desired pipetting positions are arranged for displacements above the second region 13 in order to enable pipetting of predetermined amounts of the samples from the sample containers disposed in that region.

The second region 13 can include a rack 15 for receiving components necessary for special assays, for example, assays making use of a so called ion selective electrode.

A washing position 19, where washing of the pipetting needles is carried out, is positioned adjacent to each the first region 18 and the second region 13 respectively.

Figure 2:
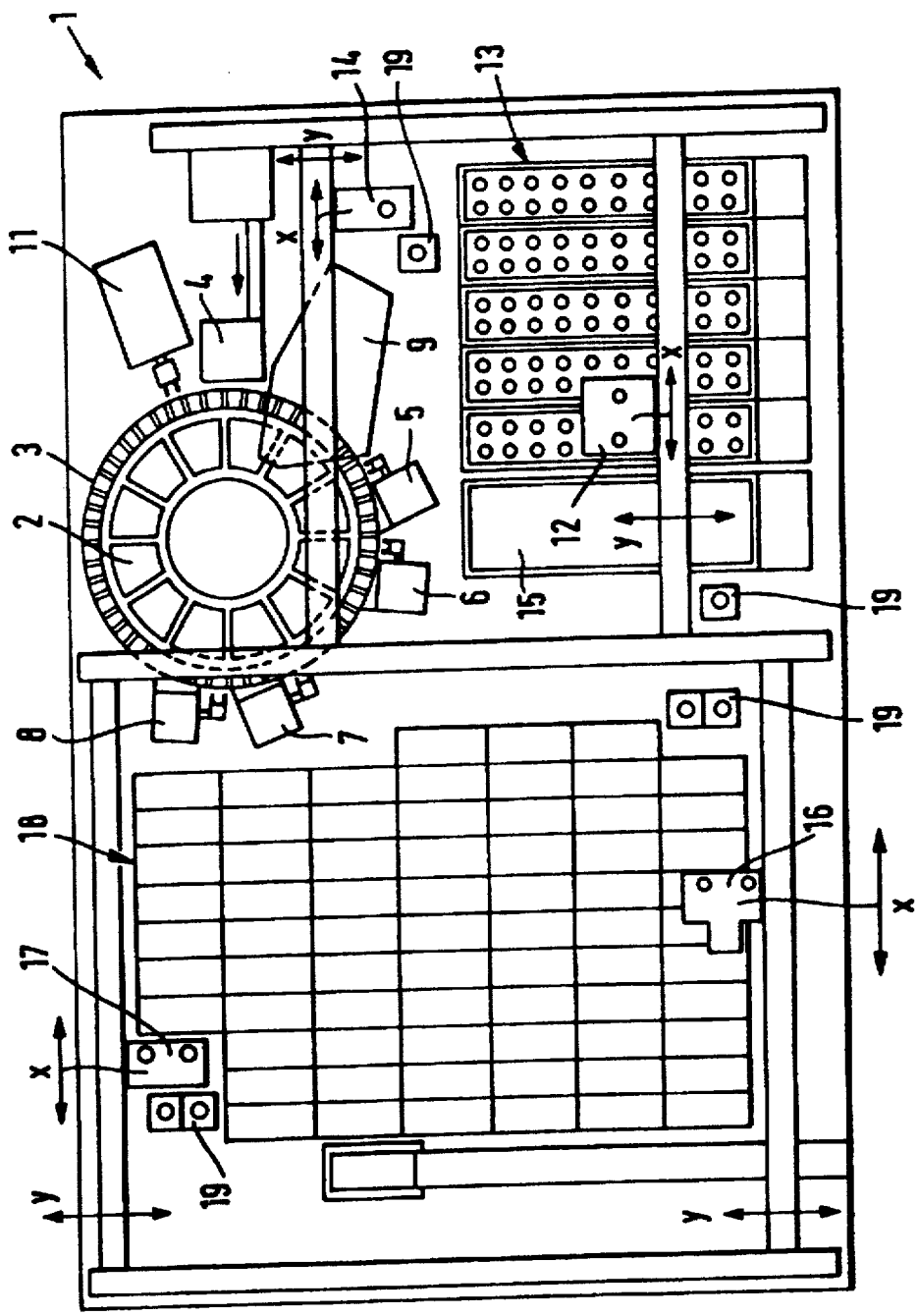
FIG. 2 is a plan view of the device in the direction of arrow I in FIG. 1.

The analytical region contains a cuvette transfer device 2 and a number of stations for processing the samples in the cuvettes. This analytical region is shown in plan view in FIG. 2. It comprises the components described hereafter.

The cuvette conveying device 2 is a circular rotor, which can be rotated by a drive (not shown) through exact angular steps in both directions of rotation. The measuring cuvettes are held on the outer edge 3 of the rotor. The measuring cuvettes have a flange on their upper surface which rests on a flat annular surface at right angles to the rotor axis, they have a wall surface which simultaneously abuts the substantially cylindrical outer surface of the rotor, and also the cuvettes are held by spring tongues which are associated with each cuvette position and project radially over the cuvettes, which for this purpose have a projection (not shown) on their underside for engaging in a recess in the cuvette flange. The resilient holder holds the cuvettes sufficiently firmly to prevent them from falling out by themselves, even when the rotor rotates. On the other hand the resilient holder enables the cuvettes to be easily withdrawn or inserted manually or by a mechanical gripping mechanism.

A detailed description of the rotor 2 and its operation is given in European Patent Application No. 92.105902. Reference is made to this description herewith.

The rotor conveys the cuvettes to a photometer 9 for making absorption measurements. The cuvettes travel through the light beam of the photometer.

Processing stations are disposed in exactly defined positions relative to the rotor. The processing stations are equipped with means for removing individual cuvettes from the rotor and/or for inserting individual cuvettes on the rotor when the rotor is not moving. The functions of the processing stations will be described in detail hereinafter. A detailed description of the processing stations for adding samples or reagents is given in European Patent Application No. 92.105901. Reference is made to this description herewith.

One processing station 4 is for insertion of new cuvettes and removal of used cuvettes at the end of analysis. The cuvettes removed from the rotor are placed in a waste container.

One processing station 8 is for metering of reagents. One of the cuvettes on the rotor is taken off and moved to a processing position in the station. One or more reagents are pipetted into the cuvette. Simultaneously, the reagents are mixed by suitably moving the cuvette, after which the cuvette and reagents are returned to the rotor.

A processing station 6 is for preliminary dilution of the sample. An empty cuvette is taken off the rotor and brought to a processing position in the station. A preset amount of sample and dilution liquid is pipetted in to the cuvette. At the same time, the dilute sample is mixed by suitably moving the cuvette, after which the cuvette is put back on the rotor.

A processing station 5 is for metering of samples. One of the cuvettes on the rotor is taken off and brought into a processing position in the station. A preset quantity of the dilute sample is pipetted into the cuvette. At the same time, the reagents are mixed by suitably moving the cuvette. The cuvette containing the mixture of samples and reagents is then returned to the rotor.

A processing station 7 is for adding a starting reagent to start the reaction by the sample. A cuvette is taken off the rotor and brought to a processing position in the station. A preset amount of starting reagent is pipetted into the cuvette. At the same time the mixture of samples and reagents is mixed by suitably moving the cuvette. The cuvette is then put back on the rotor.

A processing station 11 is for fluorescence polarimetric (FP) measurement. A sample containing a mixture of samples and reagents is taken off the rotor and brought to a measuring chamber in the station. At the end of the measurement, the cuvette is returned to the rotor.

Using measurement of absorption as an example, a determination program proceeds as follows:

To make the required determination, a processing station 4 places a cuvette on the rotor. Firstly, an air test measurement is made on the cuvette on the rotor.

Thirty seconds later, the processing station 8 takes the cuvette off the rotor and moves it into a pipetting position in the processing station, where one or more reagents are pipetted into the cuvette. When there are a number of reagents, they are mixed during and after pipetting. The cuvette is then returned to the rotor.

Seventy two seconds later, the cuvette is taken off the rotor by the processing station 6 and brought to the pipetting position, where the sample and diluent are metered by the sample transfer means. At the same time and/or afterwards, the substances are mixed and and, after the pre-dilute sample has been used, the cuvette is put back on the rotor.

Six seconds later, the processing station 5 takes the cuvette from the rotor and moves it into the pipetting position, where the sample is metered by the transfer means and then mixed and the cuvette is returned to the rotor. A to measurement is then made on the rotor.

One hundred and sixty two seconds later, the processing station 7 takes the cuvette off the rotor and brings it to the pipetting position, where a measured amount of starting reagent is added and mixed in and the cuvette is returned to the rotor.

Three hundred and twenty-four seconds later, the processing station 4 takes the cuvette off the rotor and dumps it.

While the cuvettes are on the rotor, an absorption measurement is made every six seconds.

In addition to this sequence, there are two treatment phases for fluorescence polarometric (FP) measurements.

When the cuvette is returned to the rotor after adding the sample, it is removed 132 seconds later by the processing station 11 and an FP blank measurement (parallel and at right angles) is made.

Accordingly, 90 seconds after the cuvette and the measured amount of starting reagent have been put back on the rotor, the cuvette is again removed by the processing station 11 and measured and then returned to the rotor.

During the pipetting time in the processing stations, the rotor makes a complete revolution for the absorption measurement. The photometer irradiates the cuvettes with white light, which is then divided into twelve wavelengths. Any two values of these twelve wavelengths are stored for further processing. This results in a measuring point at two wavelengths for each cuvette every six seconds.

We claim:

1. A device for chemical and/or biochemical analysis of one or more individual samples using at least one reagent, said device comprising:
    a) a plurality of individual cuvettes each for storing an individual sample therein;
    b) a first processing station for pipetting of samples into the cuvettes;
    c) a second processing station for pipetting at least one reagent into the cuvettes;
    d) a third processing station for subjecting the cuvettes to chemical and/or biochemical analysis;
    e) a conveying rotor configured to retain individual cuvettes and to rotate through angular steps in both directions of rotation and for conveying individual cuvettes to each of the processing stations, said rotor having a periphery and each processing station being arranged adjacent to the periphery; and
    f) removal means in each of the processing stations i) for removing an individual cuvette from the rotor and placing the removed individual cuvette in a predetermined position in at least one of the processing stations for processing, and ii) for returning the processed cuvette to the rotor from the processing station.

2. A device according to claim 1, wherein the removal means for removing individual cuvettes from the conveying-rotor are parts of a processing station.

* * * * *